(12) United States Patent
Cammenga et al.

(10) Patent No.: US 10,962,493 B2
(45) Date of Patent: Mar. 30, 2021

(54) NANOFIBER SMOKE DETECTION CALIBRATION

(71) Applicant: GENTEX CORPORATION, Zeeland, MI (US)

(72) Inventors: David J. Cammenga, Zeeland, MI (US); Kurtis L. Geerlings, Zeeland, MI (US); Joel C. Nemes, Holland, MI (US); William L. Tonar, Holland, MI (US); David E. Christian, Zeeland, MI (US); Darin D. Tuttle, Byron Center, MI (US); Xiaoxu Niu, Grand Rapids, MI (US)

(73) Assignee: GENTEX CORPORATION, Zeeland, MI (US)

( * ) Notice: Subject to any disclaimer, the term of this patent is extended or adjusted under 35 U.S.C. 154(b) by 53 days.

(21) Appl. No.: 16/387,593

(22) Filed: Apr. 18, 2019

(65) Prior Publication Data
US 2019/0323979 A1 Oct. 24, 2019

Related U.S. Application Data

(60) Provisional application No. 62/659,293, filed on Apr. 18, 2018.

(51) Int. Cl.
*G01N 27/12* (2006.01)
*G01N 33/00* (2006.01)

(52) U.S. Cl.
CPC ......... *G01N 27/127* (2013.01); *G01N 27/122* (2013.01); *G01N 27/126* (2013.01); *G01N 33/0063* (2013.01)

(58) Field of Classification Search
None
See application file for complete search history.

(56) References Cited

U.S. PATENT DOCUMENTS

| 4,839,527 A | 6/1989 | Leitch |
| 2012/0092175 A1 | 4/2012 | Adams et al. |
| 2014/0235493 A1* | 8/2014 | Zang ................. G01N 33/0031 506/9 |

FOREIGN PATENT DOCUMENTS

RU  2317940 C1  2/2008

OTHER PUBLICATIONS

International Search Research dated Aug. 8, 2019, for corresponding PCT application No. PCT/US 2019/028013, 2 pages.

(Continued)

*Primary Examiner* — Jas A Sanghera
(74) *Attorney, Agent, or Firm* — Price Heneveld LLP; Bradley D. Johnson

(57) ABSTRACT

A detector is provided including a plurality of nanofiber chemical sensors, each having an electrical characteristic; and a processing and alarm circuit in electrical communication with the plurality of nanofiber chemical sensors; wherein the electrical characteristics of at least one of the plurality of nanofiber chemical sensors changes in the presence of a first airborne material; wherein the electrical characteristics of at least one of the plurality of nanofiber chemical sensors changes in the presence of a second airborne material; and wherein the changes in the electrical characteristics of at least one of the plurality of nanofiber chemical sensors in the presence of the first airborne material are different from the changes in the electrical characteristics of at least one of the plurality of nanofiber chemical sensors in the presence of the second airborne material.

19 Claims, 3 Drawing Sheets

(56) References Cited

OTHER PUBLICATIONS

Written Opinion of the International Searching Authority dated Aug. 8, 2019, for corresponding PCT application No. PCT/US 2019/028013, 3 pages.

International Preliminary Report on Patentability dated Oct. 20, 2020, for correspondence PCT application No. PCT/US2019/28013, 4 pages.

* cited by examiner

NANOFIBER SMOKE DETECTION CALIBRATION

CROSS REFERENCE TO RELATED APPLICATIONS

This application claims the benefit of and priority to U.S. Provisional Patent Application No. 62/659,293, filed on Apr. 18, 2018, entitled Nanofiber Smoke Detection Calibration, the entire disclosure of which is hereby incorporated herein by reference.

BACKGROUND OF THE INVENTION

The present invention generally relates to airborne particle detectors and chemical sensors, and more particularly, to nanofiber chemical sensors.

SUMMARY OF THE INVENTION

According to one aspect of the present disclosure, a detector is provided comprising a nanofiber chemical sensor for sensing a particular or specific airborne material present to be detected, the nanofiber chemical sensor having an electrical characteristic that changes in the presence of the particular airborne material. The detector may further comprise a processing and alarm circuit in electrical communication with the nanofiber chemical sensor for monitoring the electrical characteristic of the nanofiber chemical sensor and generating an alarm signal in response to a change in the electrical characteristic. The particular airborne material may be one of a combustion by-product, a chemical, a toxin, or an explosive. The nanofiber chemical sensor may be an organic conductive nanofiber chemical sensor. The detector may further comprise a photodiode, and the photodiode may be in electrical communication with the processing and alarm circuit. The detector may further comprise a light source, and the light source may be blocked from shining light directly on the photodiode.

According to another aspect of the present disclosure, a detector is provided comprising: a first nanofiber chemical sensor for sensing a first airborne material, the first nanofiber chemical sensor having an electrical characteristic that changes in the presence of the first airborne material; a second nanofiber chemical sensor for sensing a second airborne material, the second nanofiber chemical sensor having an electrical characteristic that changes in the presence of the second airborne material; and a processing and alarm circuit in electrical communication with the first and second nanofiber chemical sensors for monitoring the electrical characteristics of the first and second nanofiber chemical sensors and generating an alarm signal in response to a change in at least one of the electrical characteristics of the first and second nanofiber chemical sensors. The second airborne material may be different from the first airborne material. The second airborne material may provoke different levels of response from the second nanofiber sensor than from the first nanofiber sensor. The first and second particular airborne materials may be one or a combination of combustion by-products, chemicals, or toxins. The nanofiber chemical sensor may be an organic conductive nanofiber chemical sensor. The detector may further comprise a photodiode, and the photodiode may be in electrical communication with the processing and alarm circuit. The detector may further comprise a light source, and the light source may be blocked from shining light directly on the photodiode. Additionally or alternatively the detector may comprise an ionization detector having a radioactive ionization source that generates a current in the presence of ionized airborne chemicals, chemical compounds, or particles and is in electrical communication with the processing and alarm circuit.

According to another aspect of the present disclosure, a detector is provided comprising: a housing; an exposed nanofiber chemical sensor disposed in the housing so as to be exposed to ambient air for sensing a particular airborne material present in smoke within the ambient air, the exposed nanofiber chemical sensor having an electrical characteristic that changes in the presence of the particular airborne material; a complementary nanofiber chemical sensor for sensing the same airborne material as the exposed nanofiber chemical sensor, the complementary nanofiber chemical sensor is disposed in the housing so as to not be exposed to the ambient air; and a processing and alarm circuit for monitoring the electrical characteristics of the exposed nanofiber chemical sensor and the complementary nanofiber chemical sensor and generating an alarm signal in response to a change in the electrical characteristic of the exposed nanofiber chemical sensor relative to the same electrical characteristic in the complementary nanofiber chemical sensor. The processing and alarm circuit may comprise a processor; the processor may be coupled to receive outputs of the exposed and complementary nanofiber chemical sensors; the processor may be programmed to distinguish between one of airborne chemicals, chemical compounds, and particles from a fire and one of airborne chemicals, airborne chemical compounds, and airborne particles from a nuisance event based on the electrical characteristics of the exposed and complementary nanofiber chemical sensors. The particular airborne material may be one of a combustion by-product, a chemical, a toxin, or an explosive. The nanofiber chemical sensor and the complementary nanofiber chemical sensor may be organic conductive nanofiber chemical sensors. A water permeable membrane may be disposed so as to allow the complementary nanofiber chemical sensors to be exposed to the same relative humidity level as the exposed nanofiber chemical sensors. The water permeable membrane may be impermeable to air. The detector may further comprise a photodiode, and the photodiode may be in electrical communication with the processing and alarm circuit. The detector may further comprise a light source, and the light source may be blocked from shining light directly on the photodiode. Additionally or alternatively the detector may comprise an ionization detector having a radioactive ionization source that generates a current in the presence of ionized airborne chemicals, chemical compounds, or particles and is in electrical communication with the processing and alarm circuit.

According to another aspect of the present disclosure, a detector is provided comprising: a housing; a first exposed nanofiber chemical sensor disposed in the housing so as to be exposed to ambient air for sensing a first airborne material within the ambient air, the first exposed nanofiber chemical sensor having an electrical characteristic that changes in the presence of the first airborne material; a first complementary nanofiber chemical sensor for sensing the same first airborne material as the first exposed nanofiber chemical sensor, the first complementary nanofiber chemical sensor is disposed in the housing so as to not be exposed to the ambient air; a second exposed nanofiber chemical sensor disposed in the housing so as to be exposed to the ambient air for sensing a second airborne material, the second exposed nanofiber chemical sensor having an electrical characteristic that changes in the presence of the second airborne material; a second complementary nanofiber chemical sensor for sensing the same second airborne material as the second exposed nanofiber chemical sensor, the second complementary nanofiber chemical sensor is disposed in the housing so as to not be exposed to the ambient air; and a processing and alarm circuit for monitoring the electrical characteristics of the first and second exposed nanofiber chemical sensors and the first and second complementary nanofiber chemical sensors and generating an alarm signal in response to a change in at least one of the electrical characteristics of the first and second exposed nanofiber chemical sensors relative to the same electrical characteristic in the respective first and second complementary nanofiber chemical sensors. The second nanofiber chemical sensor may have an electrical characteristic that may change in the presence of the second airborne material. The second airborne material may be different from the first airborne material. Second airborne material may provoke different levels of response from the second nanofiber sensor than from the first nanofiber sensor. The processing and alarm circuit may comprise a processor; wherein the processor is coupled to receive outputs of the first and second exposed nanofiber chemical sensors and at least one of the first and second complementary nanofiber chemical sensors; and wherein the processor is programmed to distinguish between changes in electrical characteristics of the first and second exposed nanofiber chemical sensors triggered by drift and those triggered by a combustion event. The processor may be programmed to generate an alarm signal in response to a change in at least one of the electrical characteristics of the first and second exposed nanofiber chemical sensors relative to the same electrical characteristic in the respective first and second complementary nanofiber chemical sensors. The first and second exposed nanofiber chemical sensors and the first and second complementary nanofiber chemical sensors may be organic conductive nanofiber chemical sensors. The first and second particular airborne materials may be one or a combination of combustion by-products, chemicals, toxins, or explosives. The nanofiber chemical sensor and the complementary nanofiber chemical sensor may be organic conductive nanofiber chemical sensors. A water permeable membrane may be disposed so as to allow the complementary nanofiber chemical sensors to be exposed to the same relative humidity level as the exposed nanofiber chemical sensors. The water permeable membrane may be impermeable to air. The detector may further comprise a photodiode, and the photodiode may be in electrical communication with the processing and alarm circuit. Additionally or alternatively the detector may comprise an ionization detector having a radioactive ionization source that generates a current in the presence of ionized airborne chemicals, chemical compounds, or particles and is in electrical communication with the processing and alarm circuit.

According to another aspect of the disclosure, a detector may comprise a first nanofiber chemical sensor, the first nanofiber chemical sensor having an electrical characteristic that changes in the presence of a first airborne material; a second nanofiber chemical sensor, the second nanofiber chemical sensor having an electrical characteristic that changes in the presence of a second airborne material; a photodiode having an output and a sensitivity; and a processing and alarm circuit in electrical communication with the first and second nanofiber chemical sensors for monitoring the electrical characteristics of the first and second nanofiber chemical sensors, and in electrical communication with the photodiode; wherein the sensitivity of the photodiode may be adjusted in response to changes in the electrical characteristics of the first and second nanofiber chemical sensors. The second nanofiber chemical sensor may have an electrical characteristic that may change in the presence of the second airborne material. The second airborne material may be different from the first airborne material. Second airborne material may provoke different levels of response from the second nanofiber sensor than from the first nanofiber sensor. The processing and alarm circuit may generate an alarm signal in response to a change in the output of the photodiode.

According to another aspect of the disclosure, a detector may comprise a plurality of nanofiber chemical sensors, each having an electrical characteristic; and a processing and alarm circuit in electrical communication with the plurality of nanofiber chemical sensors; wherein the electrical characteristics of at least one of the plurality of nanofiber chemical sensors changes in the presence of a first airborne material; wherein the electrical characteristics of at least one of the plurality of nanofiber chemical sensors may change in the presence of a second airborne material; and wherein the changes in the electrical characteristics of at least one of the plurality of nanofiber chemical sensors in the presence of the first airborne material may be different from the changes in the electrical characteristics of at least one of the plurality of nanofiber chemical sensors in the presence of the second airborne material. The second nanofiber chemical sensor may have an electrical characteristic that may change in the presence of the second airborne material. The second airborne material may be different from the first airborne material. Second airborne material may provoke different levels of response from the second nanofiber sensor than from the first nanofiber sensor. The processing and alarm circuit may generate an alarm signal when the changes in electrical characteristics of the plurality of nanofiber chemical sensors indicate the presence of airborne chemicals, chemical compounds, or particles from a combustion event. The detector may further comprise a photodiode having a sensitivity; the sensitivity of the photodiode may be increased when the changes in electrical characteristics of the plurality of nanofiber chemical sensors indicate the presence of material present in a combustion event, and the sensitivity of the photodiode may be decreased when the changes in electrical characteristics of the plurality of nanofiber chemical sensors indicate the presence of airborne chemicals, chemical compounds, or particles present in a nuisance event. The detector may further comprise a housing and a plurality of complementary nanofiber chemical sensors, each having an electrical characteristic. The plurality of complementary nanofiber chemical sensors may be disposed in the housing so as to not be exposed to the ambient air. The processing and alarm circuit may be in electrical communication with the plurality of complementary nanofiber chemical sensor and may monitor changes in the electrical characteristic of the plurality of nanofiber chemical sensors relative to the same electrical characteristic in the plurality of complementary nanofiber chemical sensors. The electrical characteristics of at least one of the plurality of complementary nanofiber chemical sensors may change in the presence of a first airborne material; and the electrical characteristics of at least one of the plurality of complementary nanofiber chemical sensors may change in the presence of a second airborne material; and the changes in the electrical characteristics of at least one of the plurality of complementary nanofiber chemical sensors in the presence of the first airborne material may be different from the changes in the electrical characteristics of at least one of the plurality of nanofiber chemical sensors in the presence of the second airborne material. The second nanofiber chemical sensor may have an electrical characteristic that may change in the presence of the second airborne material. Second airborne material may be different from the first airborne material. Second airborne material may provoke different levels of response from the second nanofiber sensor than from the first nanofiber sensor. A water permeable membrane may be disposed so as to allow the complementary nanofiber chemical sensors to be exposed to the same relative humidity level as the exposed nanofiber chemical sensors. The water permeable membrane may be impermeable to air. The detector may further comprise a housing, and the photodiode, the first nanofiber chemical sensor and the second nanofiber chemical sensor may be disposed within the housing. The first and second nanofiber chemical sensors may be organic conductive nanofiber chemical sensors.

These and other features, advantages, and objects of the present invention will be further understood and appreciated by those skilled in the art by reference to the following specification, claims, and appended drawings.

BRIEF DESCRIPTION OF THE DRAWINGS

The present invention will become more fully understood from the detailed description and the accompanying drawings, wherein.

DETAILED DESCRIPTION OF THE EMBODIMENTS

Figure 3:
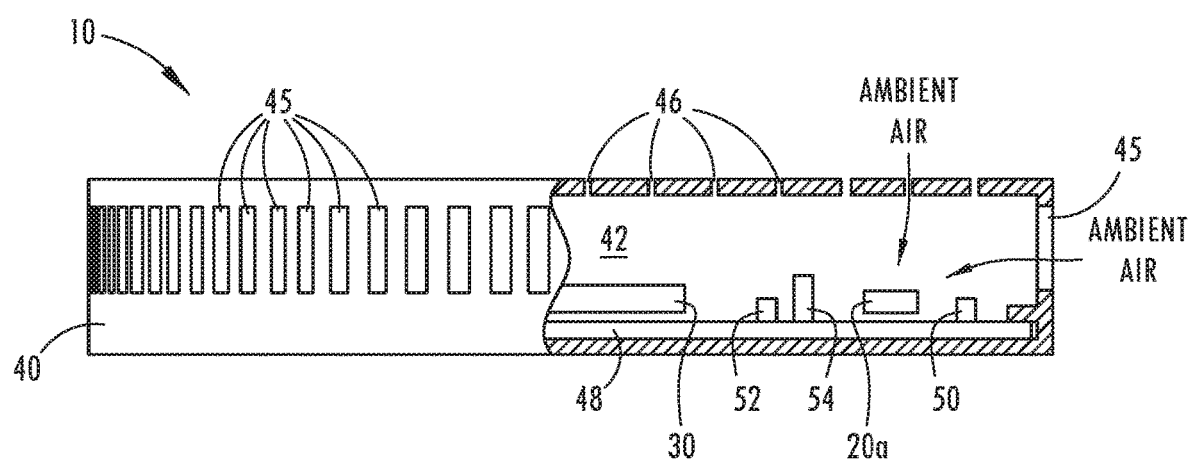
FIG. 3 is a side view of the detector of FIG. 1 shown in partial cross section.

For purposes of description herein, the terms "upper," "lower," "right," "left," "rear," "front," "vertical," "horizontal," and derivatives thereof shall relate to the invention as oriented in FIG. 3. Unless stated otherwise, the term "front" shall refer to the surface of the element closer to an intended viewer of a display, and the term "rear" shall refer to the surface of the element further from the intended viewer of the display. However, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element preceded by "comprises a . . . " does not, without more constraints, preclude the existence of additional identical elements in the process, method, article, or apparatus that comprises the element.

UL recently introduced new requirements for fire and smoke detection. There are new materials used in home construction and in the home. These materials tend to burn quicker and hotter and release combustion products that traditional smoke detectors may have difficulty detecting in the early stages of a combustion event. There are also tests of common events (food frying-toasting-broiling) that should not trigger an alarm. To pass the requirements, fire alarms must distinguish between fire or combustion events and nuisance events and respond appropriately, generating an alarm for a fire event while not generating an alarm for most nuisance events.

A smart sensor integrated into a fire or smoke alarm and configured to determine whether airborne chemicals, chemical compounds, or particles are from fires or from nuisance events may reduce false alarms while alerting building occupants to fires. The smart sensors may include organic conductive nanofiber chemical sensors, quartz crystal microbalance sensors, or other smart sensors.

An organic conductive nanofiber chemical sensor may be used to facilitate a detection of a combustion event and/or a nuisance event. The nanofibers used in these chemical sensors are synthesized with specific functional groups that can interact with airborne materials, vapors, chemicals, chemical compounds, and particles. The nanofibers have a very high 3-dimensional surface area that is able to interact with target analytes. The nanofibers are deposited on an interdigitated electrode to form an electrode-nanofiber array (hereinafter referred to as a "nanofiber chemical sensor"). The nanofibers may be doped with a light source to enhance electrical conductivity of the nanofibers. Interaction of the nanofibers with airborne materials changes the measured electrical characteristics of the nanofiber chemical sensor. An increase or decrease in an electrical characteristic, including measured current or effective resistance of the nanofiber chemical sensor, occurs as a result of these airborne material interactions.

Organic conductive nanofibers with different functional groups may have a different response to the same airborne material. By using one or more of these different nanofiber chemical sensors in an array of such nanofiber chemical sensors, a response signature can be established for a specific or particular airborne material. The nanofiber chemical sensors can be configured to detect a variety of airborne chemicals, including chemicals, toxins, combustion by-products, and explosives.

The organic conductive nanofiber-based chemical sensors can detect a combustion event and can distinguish between different combustion events based on the response signature of the sensor or sensor array in response to the presence of combustion by-products. Based on the nanofiber sensor or combination of nanofiber sensors that trigger the processing and alarm circuit, the processing and alarm circuit may be configured to determine what type of material is producing combustion by-products in the combustion event. In an embodiment, the processing and alarm circuit may be configured such that an alarm is triggered by the specific characteristic sensor response to known combustion events, but not triggered by the specific characteristic response to known nuisance events. The processing and alarm circuit may be configured to transmit that information to an external receiver.

Figure 1:
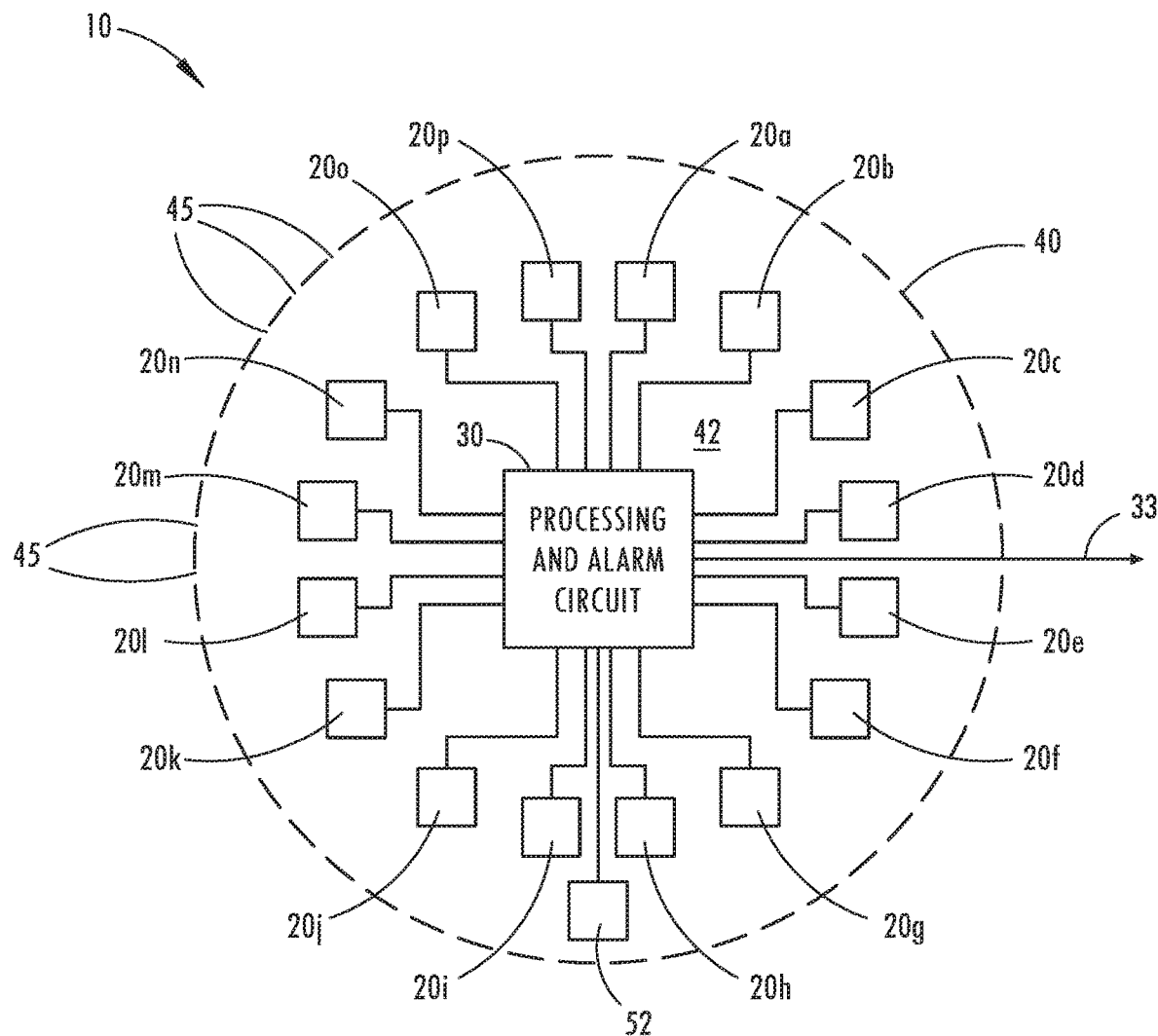
FIG. 1 is an electrical circuit diagram of a detector according to a first embodiment.

FIG. 1 shows an example of a detector 10 having a nanofiber chemical sensor 20a for sensing a particular airborne material to be detected. The term "nanofiber chemical sensor" as used herein can refer to a single nanofiber chemical sensor or to multiple nanofiber chemical sensors. The airborne material may be, for example, a combustion by-product, a chemical or chemical compound, a toxin, or an explosive. Nanofiber chemical sensor 20a has an electrical characteristic that may change, and may change a certain amount in the presence of the particular airborne material. Nanofiber chemical sensors 20a-20p should be large enough to register a measurable response to the presence of the particular airborne material.

Detector 10 further includes a processing and alarm circuit 30 in electrical communication with nanofiber chemical sensor 20a for monitoring the electrical characteristic of nanofiber chemical sensor 20a and generating an alarm signal in response to a change in the electrical characteristic. In some embodiments, as shown in FIG. 1, detector 10 may include a first nanofiber chemical sensor 20a for sensing a first airborne material where first nanofiber chemical sensor 20a has an electrical characteristic that may change in the presence of the first airborne material and a second nanofiber chemical sensor 20b for sensing a second airborne material where second nanofiber chemical sensor 20b has an electrical characteristic that may change in the presence of the second airborne material. Second airborne material may be different from the first airborne material. Second airborne material may provoke different levels of response from the second nanofiber sensor than from the first nanofiber sensor. Processing and alarm circuit 30 may be in electrical communication with first and second nanofiber chemical sensors 20a and 20b for monitoring the electrical characteristics of first and second nanofiber chemical sensors 20a and 20b and generating an alarm signal in response to a change in at least one of the electrical characteristics of at least one of first and second nanofiber chemical sensors 20a and 20b. Moreover, a plurality of such nanofiber chemical sensors 20a-20p may be provided. Each nanofiber chemical sensor 20a-20p may be configured to sense different airborne materials.

In some embodiments, detector 10 may include at least a first nanofiber chemical sensor 20a, and a second nanofiber chemical sensor 20b. At least one of first nanofiber chemical sensor 20a and second nanofiber chemical sensor 20b may respond with changes in electrical characteristics to the presence of a first airborne material, and at least one of the first and second nanofiber chemical sensors 20a, 20b may respond with changes in electrical characteristics to the presence of a second airborne material. However, the changes in the electrical characteristics of at least one of the first and second nanofiber chemical sensors 20a, 20b in the presence of the first airborne material may be different from the changes in the electrical characteristics of at least one of the first and second nanofiber chemical sensors 20a, 20b in the presence of the second airborne material. In some embodiments, a plurality of such nanofiber chemical sensors 20a-20p may be provided. Different airborne materials may provoke a different combination of responses in the plurality of nanofiber chemical sensors 20a-20p, thereby allowing detector 10 to differentiate between different airborne materials and determine whether the airborne material or materials result from a nuisance event or a combustion event.

In an embodiment, at least one of nanofiber chemical sensors 20a-20p may be operable to trigger a change in an electrical characteristic in the presence of smoke or the presence of airborne chemicals, chemical compounds, or particles that result from certain combustion events. In particular, nanofiber chemical sensors 20a-20p may be operable to trigger a change in an electrical characteristic in the presence of chemicals, chemical compounds, or particles resulting from combustion of fibers or building materials that may be present in a building or interior fire. Processing and alarm circuit 30 may be in electrical communication with each of nanofiber chemical sensors 20a-20p to detect the presence of chemicals representing a fire or combustion event based on the electrical characteristics of any one or more of the plurality of nanofiber chemical sensors 20a-20p. In some embodiments, the presence of airborne chemicals, chemical compounds, or particles associated with a combustion event may trigger an alarm in processing and alarm circuit 30. The alarm may be an audible alarm, a visual alarm, a haptic alarm such as a vibration, or a combination of these. The alarm may be sent as an alert to a remote device such as a cell phone or a computer. The alarm may be sent as an alert to first responders or other chosen recipients.

Nanofiber chemical sensors 20a-20p may be functionalized to have a different response or no response to the presence of airborne chemicals, chemical compounds, or particles resulting from nuisance events. In the presence of airborne chemicals, chemical compounds, or particles from nuisance events, processing and alarm circuit 30 may be triggered to produce a different alarm than is produced by a combustion event, or processing and alarm circuit 30 may not be triggered to produce an alarm.

In an embodiment, nanofiber chemical sensors 20a-20p may be operable to respond to the presence of particular airborne chemicals. A change in the electrical characteristics that indicates the presence of airborne chemicals may cause the processing and alarm circuit 30 to trigger an alarm. The alarm circuit 30 may also include instructions to, for example, close an automatic valve to prevent further release of the particular chemical.

In an embodiment, nanofiber chemical sensors 20a-20p may be operable to respond to the presence of airborne chemicals, chemical compounds, or particles associated with a toxin or a plurality of toxins. A change in the electrical characteristics that indicates the presence of airborne chemicals, chemical compounds, or particles associated with a toxin or toxins may cause the processing and alarm circuit 30 to trigger an alarm. The alarm may be conveyed to those in the vicinity of nanofiber chemical sensors 20a-20p. Alternatively or in addition, the alarm may be transmitted to recipients in a remote location. The alarm may be tied in with other alarm or security circuits, and may trigger a variety of different responses.

In some embodiments, the weight or mass of nanofiber chemical sensors 20a-20p may change in the presence of particular airborne chemicals. The weight or mass of nanofiber chemical sensors 20a-20p may increase or decrease, and they may increase for certain chemicals, chemical compounds, or particles and decrease for others. In some embodiments, detector 10 may comprise at least one mass sensor (not shown), and the at least one mass sensor may be configured to monitor changes in the weight or mass of nanofiber chemical sensors 20a-20p. In some embodiments, the at least one mass sensor may be capable of measuring whether there is a change in mass that exceeds a threshold level. The at least one mass sensor may communicate with detector 10 when there are changes in mass of at least one nanofiber chemical sensor 20a-20p.

In some embodiments, the visible color or absorption spectra in the infrared or ultraviolet range of nanofiber chemical sensors 20a-20p may change in the presence of particular airborne chemicals. Detector 10 may comprise at least one light absorption sensor (not shown) configured to monitor color or light absorption of nanofiber chemical sensors 20a-20p. Upon detection of a change in color of at least one of nanofiber chemical sensors 20a-20p, the at least one light absorption sensor may communicate with detector 10.

The plurality of nanofiber chemical sensors 20a-20p may be arranged in any manner and may be disposed in a first inner chamber 42 of a housing 40 having a plurality of air vents 45 for permitting ambient air to flow into first inner chamber 42 so that nanofiber chemical sensors 20a-20p are exposed to air. Air vents 45 should be large enough and/or numerous enough to allow the ambient air to flow into first inner chamber 42 without restriction.

In some embodiments, a fan, blower, Venturi air mover, an air pump, or similar fluid moving device, may be disposed in housing 40. The fluid moving device may be positioned to cause air or another fluid to flow past nanofiber chemical sensors 20a-20p. The fluid moving device may be in electrical communication with a power source. The fluid moving device may be operated automatically or may be controllable by a user. The fluid moving device may have a single speed or may have variable speeds.

In some embodiments, housing 40 may be configured to be removably or permanently mounted to a surface. Housing 40 may be mountable on a surface such as a wall or ceiling. In some embodiments, housing 40 may be small enough and light enough to be wearable by a user, and may be fastenable to a user's garments. In some embodiments, housing 40 may be configured to be handheld, and may have a handle or strap for ease of carrying.

As also shown in FIG. 1, processing and alarm circuit 30 of detector 10 may be configured to include a connection 33 to other components of a fire detection system such as smoke detectors, one or more notification appliances, and any control panels or subpanels of the system. Connection 33 may be wired or wireless.

Figure 2:
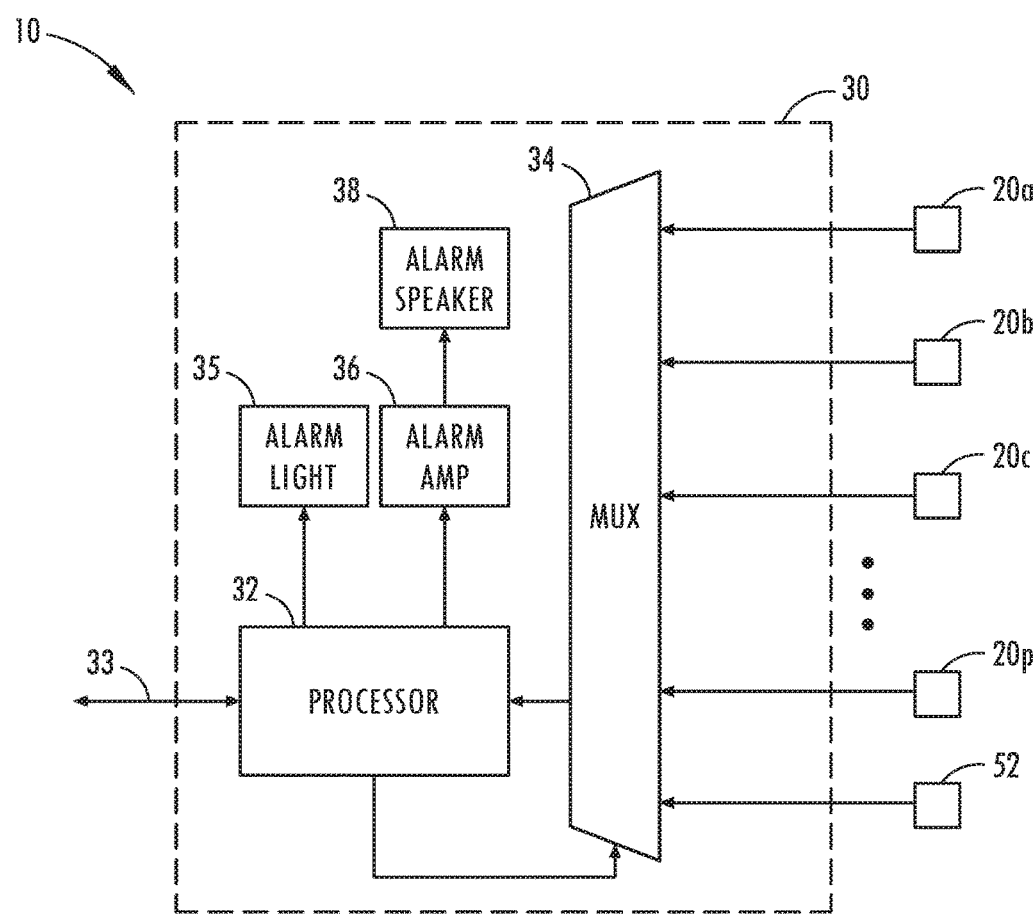
FIG. 2 is an electrical circuit diagram of the detector of FIG. 1 showing additional details of the processing and alarm circuit.

FIG. 2 is an electrical circuit diagram of detector 10 shown in FIG. 1 with additional details of processing and alarm circuit 30, which may include a processor 32 such as a microprocessor that is coupled to receive the outputs of nanofiber chemical sensors 20a-20p. Depending upon the number of nanofiber chemical sensors 20a-20p in detector 10, a multiplexer may optionally be provided to receive the outputs of nanofiber chemical sensors 20a-20p and to serially communicate those outputs to an input terminal of processor 32.

Detector 10 may also optionally include a wired or wireless connection 33 for communicating with other airborne particle detectors, smoke detectors, and/or other components of a fire detection system. For example, the system may include dedicated notification appliances that issue visual and audible alarms when airborne chemicals, chemical compounds, or particles indicative of a combustion event are detected by any one of a plurality of detectors 10 or smoke detectors that may be provided throughout a building. When used with such notification appliances, it may be optional for detectors 10 to include their own alarm light 35 and/or alarm amplifier 36 and alarm speaker 38. Otherwise, detectors 10 may include these alarm mechanisms that are controlled by processor 32 when the outputs of nanofiber chemical sensors 20a-20p detect, for example, airborne materials that are indicative of a fire or combustion event. Processor 32 may also activate alarm mechanisms 35 and 38 when a signal is received over connection 33 from another detector 10, smoke detector or other component of a fire detection system. The alarm may be configured to trigger off a specific magnitude of change in signal response of a sensor or an array of sensors.

FIG. 3 is a side view of detector 10 shown in partial cross section. FIG. 3 further illustrates the relation of air vents 45 in the sides of housing 40 and first inner chamber 42 in which nanofiber chemical sensors 20a-20p are located. As shown, additional air vents 46 may be provided in the top surface of detector 10 to provide additional air flow to nanofiber chemical sensors 20a-20p. As mentioned above, air vents 45 and 46 should be configured to minimize any restriction on airflow into first inner chamber 42.

Although processing and alarm circuit 30 and nanofiber chemical sensors 20a-20p are shown in FIG. 3 as being mounted on a common circuit board 48, they may be mounted on separate circuit boards.

In some embodiments, detector 10 may also comprise a light source such as a light emitting diode 50, and light source 50 may be mounted on printed circuit board 48. Detector 10 may also comprise a light sensing means, such as a photocell or a photodiode 52. According to some embodiments, photodiode or photocell 52 may be a silicon photodiode, and photodiode 52 may be physically optimized for generating electrical current in response to light. Photodiode 52 may be in communication with processing and alarm circuit 30 for monitoring for the presence of airborne chemicals, chemical compounds, or particles.

Photodiode or photocell 52 may be protected from ambient light. In some embodiments, an optic block 54 may prevent light generated by light source 50 from directly shining on photodiode 52, thereby allowing photodiode 52 to pick up only light scattered from airborne particulate matter. In some embodiments, light source 50 may be secured to printed circuit board 48, and printed circuit board 48 may act, at least in part, as an optic block. In some embodiments, photodiode 52 may be in a recess of the detector 10, and an optic block 54 may be disposed to prevent light generated by light source 50 from shining directly onto photodiode 52. Photodiode 52 may cause processing and alarm circuit 30 to produce an alarm based on a predetermined amount of light detected by photodiode 52.

In some embodiments, detector 10 may be configured to adjust a sensitivity of photodiode 52 so that it triggers the processing and alarm circuit 30 at either higher or lower levels of detected light than it would otherwise. Detector 10 may adjust the sensitivity of photodiode 52 based on changes in measured electrical characteristics of at least one nanofiber chemical sensors 20a-20p. This may allow for dynamic changes in sensitivity of the particle detector to not only resist nuisance alarms in the case of non-hazardous events but also provide adequate sensitivity under certain conditions where the particle detector may have low efficacy.

For example, nanofiber chemical sensors 20a-20p may each exhibit a first set of distinctive changes in electrical characteristics upon exposure to combustion by-products from a first material and a second set of distinctive changes in electrical characteristics upon exposure to combustion by-products from a second material. First material may be a material that commonly triggers a nuisance alarm in a smoke detector, and second material may be a material that is commonly produced from the combustion of material used in furniture or building construction. In some embodiments, upon sensing the first set of distinctive changes in electrical characteristics, detector 10 may adjust the sensitivity of photodiode 52 to be less sensitive, thereby making it less likely that detector 10 will trigger the processing and alarm circuit 30. Conversely, upon sensing the second set of distinctive changes in electrical characteristics, detector 10 may adjust the sensitivity of photodiode 52 to be more sensitive. In the latter case, a lower concentration of the combustion by-products of the second material may trigger the activation of processing and alarm circuit 30.

In some embodiments, a change in mass of at least one of nanofiber chemical sensors 20a-20p may cause detector 10 to trigger a change in the sensitivity of photodiode 52. In some embodiments, a change in the visible color or absorption spectra of nanofiber chemical sensors 20a-20p may cause detector 10 to trigger a change in the sensitivity of photodiode 52. Certain changes in either the mass sensor or the light absorption sensor may cause the sensitivity of photodiode 52 to become more sensitive, while other changes in either the mass sensor or the light absorption sensor may cause the sensitivity of photodiode 52 to become less sensitive.

Adjusting the sensitivity of photodiode 52 may comprise requiring a different magnitude of change in an output of photodiode to trigger the activation of processing and alarm circuit 30. After an adjustment, the changes in electrical characteristics required to trigger the activation of processing and alarm circuit 30 may be higher or lower than the original required changes in electrical characteristics.

In some embodiments, detector 10 may further comprise an ionization detector (not shown). Ionization detector may comprise an ionization chamber comprising two metal plates having a small amount of radioactive material disposed between the plates. The radioactive material may ionize the air in the ionization chamber. The plates may be configured to have a current pass between them. Airborne chemicals, chemical compounds, or particles may attach themselves to ions within the chamber, thereby decreasing the conductivity of air in the chamber. Ionization detector may be in communication with processing and alarm circuit for monitoring the presence of airborne chemicals, chemical compounds, or particles. When the conductivity has decreased a pre-set amount, an alarm may be triggered. In some embodiments, upon sensing a set of distinctive changes in electrical characteristics in nanofiber chemical sensors 20a-20p, detector 10 may adjust the sensitivity of photodiode 52 to require a different magnitude of change in conductivity of air in the chamber of ionization detector to trigger the activation of processing and alarm circuit 30. Detector 10 may be configured to adjust the sensitivity of the ionization detector so that it triggers the processing and alarm circuit 30 at either higher or lower levels than it would have otherwise. After an adjustment, the magnitude of changes in conductivity of air within the chamber required to trigger the activation of processing and alarm circuit 30 may be higher or lower than the originally required changes.

The nanofibers in nanofiber chemical sensors 20a-20p may become fouled over time. The fouling may be from particulates and other contaminants present in ambient air. To reduce or prevent fouling, in some embodiments, a filter (not shown) may be disposed in proximity to nanofiber chemical sensors 20a-20p. The filter may be, for example, a HEPA filter, a nanofiber mat filter, or any suitable filter material known to those with skill in the art. In some embodiments, the filter may be disposed to cover air vents 45, 46, either from inside or outside housing 45, to prevent or reduce the amount of foulants from entering inner chamber 42 of housing 45. In some embodiments, the filter may be disposed to surround nanofiber chemical sensors 20a-20p, thereby reducing or preventing fouling.

The nanofibers in nanofiber chemical sensors 20a-20p may degrade upon exposure to moisture. In some embodiments, a moisture shield (not shown) may be used to prevent or reduce the exposure of nanofiber chemical sensors 20a-20p to moisture. The moisture shield may be, for example, a tight mesh Teflon® or siliconized fabric screen, or any suitable filter material known to those with skill in the art that would let air flow freely through the moisture shield but would prevent or reduce the presence of moisture at nanofiber chemical sensors 20a-20p. In some embodiments, the moisture shield may be disposed to cover air vents 45, 46, either from inside or outside housing 45, to prevent or reduce the amount of moisture entering inner chamber 42 of housing 45. In some embodiments, the moisture shield may be disposed to surround nanofiber chemical sensors 20a-20p, thereby reducing or preventing moisture contacting nanofiber chemical sensors 20a-20p.

The nanofibers in nanofiber chemical sensors 20a-20p may degrade over time. This may affect the electrical properties of the nanofibers and thereby affect the ability of nanofiber chemical sensors 20a-20p to accurately sense the targeted airborne material or, when detectors are used to detect combustion events, to distinguish nuisance events from combustion events. For example, the electrical resistance of the nanofibers may increase when exposed to a specific target chemical, which causes a decrease in output current when a bias voltage is applied to the nanofibers. When the output current reaches a fixed threshold, the chemical sensor may determine that the target airborne material is present. However, the electrical resistance may also increase as the nanofibers degrade, which may make it difficult to distinguish degradation of the nanofiber from the presence of the target material. To address this problem, two of the same functional nanofiber sensor types can be used in one device. A first nanofiber chemical sensor may be positioned in "clean air" and a second nanofiber chemical sensor may be positioned in the ambient environment where it may be exposed to smoke, explosives, toxins, chemicals, chemical compounds, or other airborne particles of interest. The alarm may then be triggered based on a change in the response of one sensor versus the other. In other words, the outputs of the first and second sensors may be compared and a difference in the outputs may trigger an alarm. Alternately, the threshold current to which the output current of the first sensor is compared (to determine if a target chemical is detected) may be calibrated based on the output current of the second sensor, which is positioned in the "clean air" portion of detector 10. An example of such an arrangement is shown in FIGS. 4 and 5 and discussed below.

Figure 4:
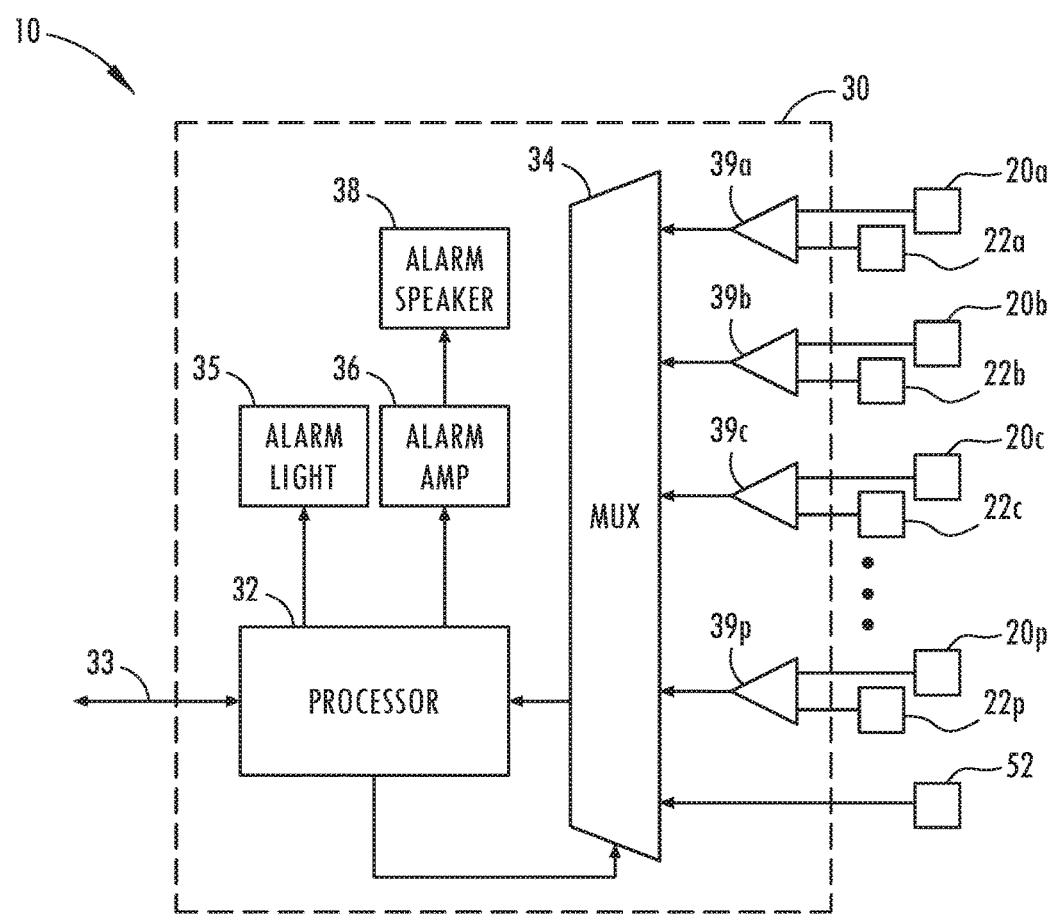
FIG. 4 is an electrical circuit diagram of a detector according to a second embodiment.
Figure 5:
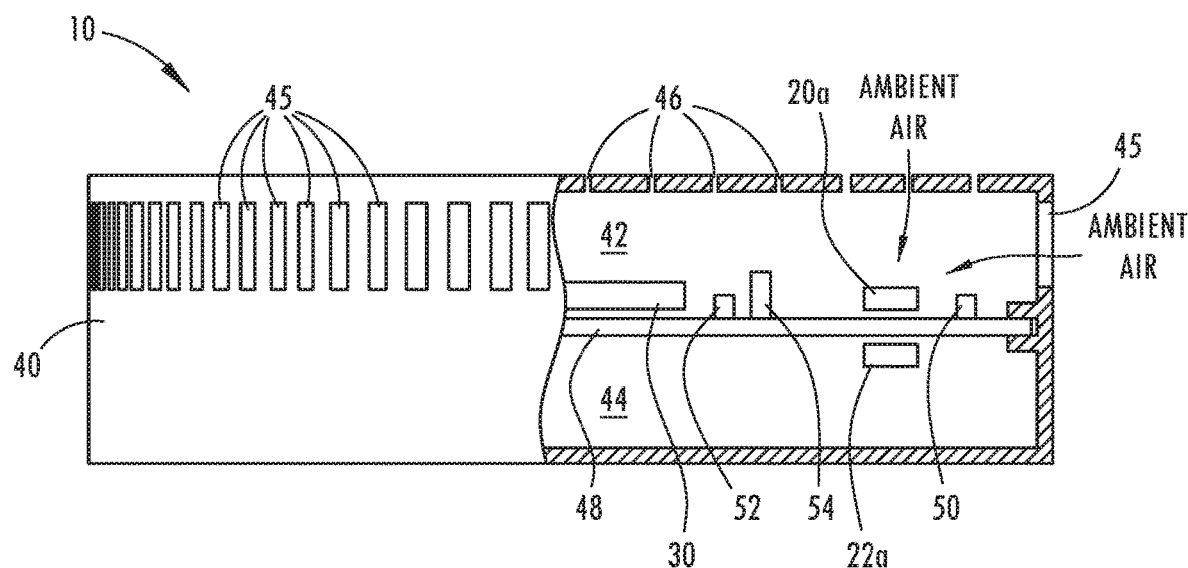
FIG. 5 is a side view of the detector of FIG. 4 shown in partial cross section.

As shown in FIG. 4, the configuration of detector 10 remains the same with the exception that a complementary nanofiber chemical sensor 22a is provided that has the same functional configuration as nanofiber chemical sensor 20a so as to sense the same airborne material. When more than one nanofiber chemical sensors 20a-20p is provided, there is a respective complementary nanofiber chemical sensor 22a-22p for each nanofiber chemical sensors 20a-20p with each complementary nanofiber chemical sensor 22a-22p configured to sense the same material as a corresponding one of nanofiber chemical sensors 20a-20p. As shown in FIG. 5, complementary nanofiber chemical sensors 22a-22p are disposed in a second inner chamber 44 of the housing 40 that is isolated from first inner chamber 42 in such a way that ambient air flows into first inner chamber 42 as previously described, but cannot flow into second inner chamber 44. Specifically, air vents 45 and 46 are provided at an upper portion of housing 40, but not in the lower portion and printed circuit board 48 (or some other structure) blocks the internal flow of air between inner chambers 42 and 44.

By providing complementary nanofiber chemical sensors 22a-22p in the manner described above, the outputs of nanofiber chemical sensors 22a-22p may be used as a baseline for comparing to the outputs of corresponding nanofiber chemical sensors 20a-20p or otherwise calibrating the respective thresholds used by processing and alarm circuit 30 to determine if the electrical characteristics of nanofiber chemical sensors 20a-20p have changed to the degree that an alarm should be triggered.

Referring back to FIG. 4, to accommodate the outputs of complementary nanofiber chemical sensors 22a-22p, processing and alarm circuit 30 may be modified to include a comparator 39a-39p (or similar circuitry) for each pair of nanofiber chemical sensors 20a-20p and complementary nanofiber chemical sensors 22a-22p. Thus, for example, comparator 39a may compare the outputs of nanofiber chemical sensor 20a and complementary nanofiber chemical sensor 22a. Comparator 39a would thus generate an output when the output of nanofiber chemical sensor 20a changes relative to complementary nanofiber chemical sensor 22a. The output of comparator 39a may then be provided to an input terminal of processor 32 or first to multiplexer 34. Because nanofiber chemical sensor 20a and complementary nanofiber chemical sensor 22a have the same construction, they would degrade at the same rate. By shielding complementary nanofiber chemical sensor 22a from ambient air, it is possible to distinguish gradual changes in the electrical characteristics due to degradation and a change occurring due to the presence of the target material in the ambient air.

Although the outputs of nanofiber chemical sensors 20a-20p and complementary nanofiber chemical sensors 22a-22p are shown as being compared in FIG. 4, the outputs of nanofiber chemical sensors 20a-20p and complementary nanofiber chemical sensors 22a-22p may be supplied to processor 32, which may use the outputs of complementary nanofiber chemical sensors 22a-22p to dynamically adjust the thresholds to which the outputs of the exposed nanofiber chemical sensors 20a-20p are compared so as to calibrate and thereby account for changes in the outputs of nanofiber chemical sensors 20a-20p occurring due to degradation.

As a variation of the embodiment shown in FIGS. 4 and 5, ambient air may be vented through printed circuit board 48 (or other structure) from first inner chamber 42 to second inner chamber 44 to expose complementary nanofiber chemical sensors 22a-22p further up the air stream such that there is a time delay in the response of complementary nanofiber chemical sensors 22a-22p relative to the response of nanofiber chemical sensors 20a-20p that triggers an alarm.

It may be desirable to expose exposed nanofiber chemical sensors 20a-20p to the same relative humidity levels as complementary nanofiber chemical sensors 22a-22p. Therefore, in some embodiments, a water permeable membrane (not shown) may be disposed so as to allow complementary nanofiber chemical sensors 22a-22p to be exposed to the same relative humidity level as exposed nanofiber chemical sensors 20a-20p. The water permeable membrane may be impermeable to air, thereby allowing the complementary nanofiber chemical sensors to remain protected. The water permeable membrane may be, for example, a polyvinyl acetate or NAFION®.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

What is claimed is:

1. A detector comprising:
a housing;
an exposed nanofiber chemical sensor disposed in the housing so as to be exposed to ambient air, the exposed nanofiber chemical sensor having an electrical characteristic that changes in the presence of a particular airborne material;
a complementary nanofiber chemical sensor having an electrical characteristic that changes in the presence of the particular airborne material, the complementary nanofiber chemical sensor disposed in the housing so as to not be exposed to the ambient air; and a processing and alarm circuit for monitoring the electrical characteristics of the exposed nanofiber chemical sensor and the complementary nanofiber chemical sensor in communication with the exposed nanofiber chemical sensor and the complementary nanofiber chemical sensor.

2. The detector of claim 1, wherein the processing and alarm circuit is configured to generate an alarm signal in response to a change in the electrical characteristic of the exposed nanofiber chemical sensor relative to the same electrical characteristic in the complementary nanofiber chemical sensor.

3. The detector of claim 1, wherein the exposed nanofiber chemical sensor and the complementary nanofiber chemical sensor are organic conductive nanofiber chemical sensors.

4. The detector of claim 1, wherein the particular airborne material is a combustion by-product.

5. The detector of claim 1, further comprising a photodiode, wherein the photodiode is in electrical communication with the processing and alarm circuit.

6. A detector comprising:
   a housing;
   a first exposed nanofiber chemical sensor disposed in the housing so as to be exposed to ambient air, the first exposed nanofiber chemical sensor having an electrical characteristic that changes in the presence of a first airborne material;
   a first complementary nanofiber chemical sensor disposed in the housing so as to not be exposed to the ambient air, the first complementary nanofiber chemical sensor having an electrical characteristic that changes in the presence of the first airborne material;
a second exposed nanofiber chemical sensor disposed in the housing so as to be exposed to the ambient air, the second exposed nanofiber chemical sensor having an electrical characteristic that changes in the presence of a second airborne material;
a second complementary nanofiber chemical sensor disposed in the housing so as to not be exposed to the ambient air, the second complementary nanofiber chemical sensor having an electrical characteristic that changes in the presence of the second airborne material; and
   a processing and alarm circuit in communication with the first and second exposed nanofiber chemical sensors and at least one of the first and second complementary nanofiber chemical sensors.

7. The detector of claim 6, wherein the processing and alarm circuit comprises a processor;
   wherein the processor is coupled to receive outputs of the first and second exposed nanofiber chemical sensors and at least one of the first and second complementary nanofiber chemical sensors; and
   wherein the processor is programmed to distinguish between changes in electrical characteristics triggered by drift of the first and second exposed nanofiber chemical sensors and those triggered by a combustion event.

8. The detector of claim 6, wherein the processor processing and alarm circuit is programmed to generate an alarm signal in response to a change in at least one of the electrical characteristics of the first and second exposed nanofiber chemical sensors relative to the same electrical characteristic in the respective first and second complementary nanofiber chemical sensors.

9. The detector of claim 6, wherein the first and second exposed nanofiber chemical sensors and the first and second complementary nanofiber chemical sensors are organic conductive nanofiber chemical sensors.

10. The detector of claim 6, wherein the first and second airborne materials are combustion by-products.

11. The detector of claim 6, further comprising a photodiode, wherein the photodiode is in electrical communication with the processing and alarm circuit.

12. A detector comprising:
   a photodiode;
   a first nanofiber chemical sensor having an electrical characteristic that changes in the presence of a first airborne material;
   a second nanofiber chemical sensor having an electrical characteristic that changes in the presence of a second airborne material; and
   a processing and alarm circuit in electrical communication with the first and second nanofiber chemical sensors for monitoring the electrical characteristics of the first and second nanofiber chemical sensors, and in electrical communication with the photodiode;
   wherein the sensitivity of the photodiode is able to be adjusted in response to changes in the electrical characteristics of at least one of the first and second nanofiber chemical sensors.

13. The detector of claim 12, wherein the photodiode has an output and a sensitivity; and wherein the sensitivity of the photodiode is increased when the change in electrical characteristics of the first and second nanofiber chemical sensors indicate the presence of one of airborne chemicals, airborne chemical compounds, and airborne particles from a combustion event.

14. The detector of claim 12, wherein the photodiode has an output and a sensitivity; and wherein the sensitivity of the photodiode is decreased when the change in electrical characteristics of the first and second nanofiber chemical sensors indicate the presence of material present in a nuisance event.

15. The detector of claim 12, further comprising at least one mass sensor in communication with at least one nanofiber chemical sensor and configured to measure a mass of at least one nanofiber chemical sensor; wherein the sensitivity of the photodiode is capable of being adjusted in response to changes in the mass of the at least one nanofiber chemical sensor.

16. The detector of claim 12, further comprising a light absorption sensor in communication with at least one nanofiber chemical sensor; wherein the sensitivity of the photodiode is capable of being adjusted in response to changes in the light absorption spectrum of the at least one nanofiber chemical sensor.

17. The detector of claim 12, wherein the processing and alarm circuit generates an alarm signal in response to a change in the output of the photodiode.

18. The detector of claim 12, wherein the first and second nanofiber chemical sensors are organic conductive nanofiber chemical sensors.

19. The detector of claim 12, further comprising a housing; wherein the photodiode, the first nanofiber chemical sensor and the second nanofiber chemical sensor are disposed within the housing.

* * * * *

UNITED STATES PATENT AND TRADEMARK OFFICE
CERTIFICATE OF CORRECTION

PATENT NO. : 10,962,493 B2  
APPLICATION NO. : 16/387593  
DATED : March 30, 2021  
INVENTOR(S) : David J. Cammenga et al.

Page 1 of 1

It is certified that error appears in the above-identified patent and that said Letters Patent is hereby corrected as shown below:

On the Title Page

Item (72) Inventors: Insert:
--(72)   Inventors: David J. Cammenga, Zeeland, MI (US);
Kurtis L. Geerlings, Zeeland, MI (US);
Joel C. Nemes, Holland, MI (US);
William L. Tonar, Holland, MI (US);
David E. Christian, Zeeland, MI (US);
Darin D. Tuttle, Byron Center, MI (US);
Xiaoxu Niu, Grand Rapids, MI (US);
Nichole A. Crane, Salt Lake City, UT (US);
Benjamin R. Bunes, Murray, UT (US);
Ross A. Riches, Sandy, UT (US);
Douglas W. Later, Sandy, UT (US)--

Signed and Sealed this  
Seventeenth Day of May, 2022

Katherine Kelly Vidal  
*Director of the United States Patent and Trademark Office*